(12) United States Patent  
Glattstein et al.

(10) Patent No.: US 7,829,019 B2
(45) Date of Patent: Nov. 9, 2010

(54) MOLDED CASING FOR A TEST KIT

(75) Inventors: Baruch Glattstein, Jerusalem (IL); Shmuel Huss, Jerusalem (IL); Mordechai Brestel, Rehovot (IL)

(73) Assignee: Identa Ltd., Jerusalem (IL)

( * ) Notice: Subject to any disclaimer, the term of this patent is extended or adjusted under 35 U.S.C. 154(b) by 1147 days.

(21) Appl. No.: 10/836,341

(22) Filed: May 3, 2004

(65) Prior Publication Data

US 2004/0202572 A1    Oct. 14, 2004

Related U.S. Application Data

(63) Continuation of application No. 09/809,428, filed on Mar. 16, 2001, now abandoned.

(51) Int. Cl.
*G01N 33/00*    (2006.01)
(52) U.S. Cl. .............................. 422/58; 422/50; 422/55; 422/56; 422/57; 422/99; 422/100; 422/102
(58) Field of Classification Search .................. 422/50, 422/55, 56, 57, 58, 99, 100, 102
See application file for complete search history.

(56) References Cited

U.S. PATENT DOCUMENTS

| 4,732,850 A | 3/1988 | Brown et al. |
| 5,418,167 A | 5/1995 | Matner et al. |
| 5,817,522 A | 10/1998 | Goodman et al. |
| 6,043,097 A | 3/2000 | Dumitrescu et al. |

*Primary Examiner*—Sam P Siefke
(74) *Attorney, Agent, or Firm*—Lowe Hauptman Ham & Berner LLP

(57) ABSTRACT

A casing for use as a test kit that employs crushable ampoules prefilled with chemical or biological reagents, comprising a molded casing having a distinct reaction chamber, and at least one distinct cell adapted for receiving a crushable ampoule. The cell has a flexible pressing area at its outer wall for pressing and crushing the ampoule. An opening exists between the chamber and the cell that is either narrow enough, or provided with filtering means so as to allow passage of the reagent while preventing passage of glass shards from the cell to the chamber. The casing further comprises an inlet leading from the exterior of the casing into the inner space of the reaction chamber and a sampling probe, for enabling obtaining samples of material and delivery of said material through the inlet to the reaction chamber.

21 Claims, 3 Drawing Sheets

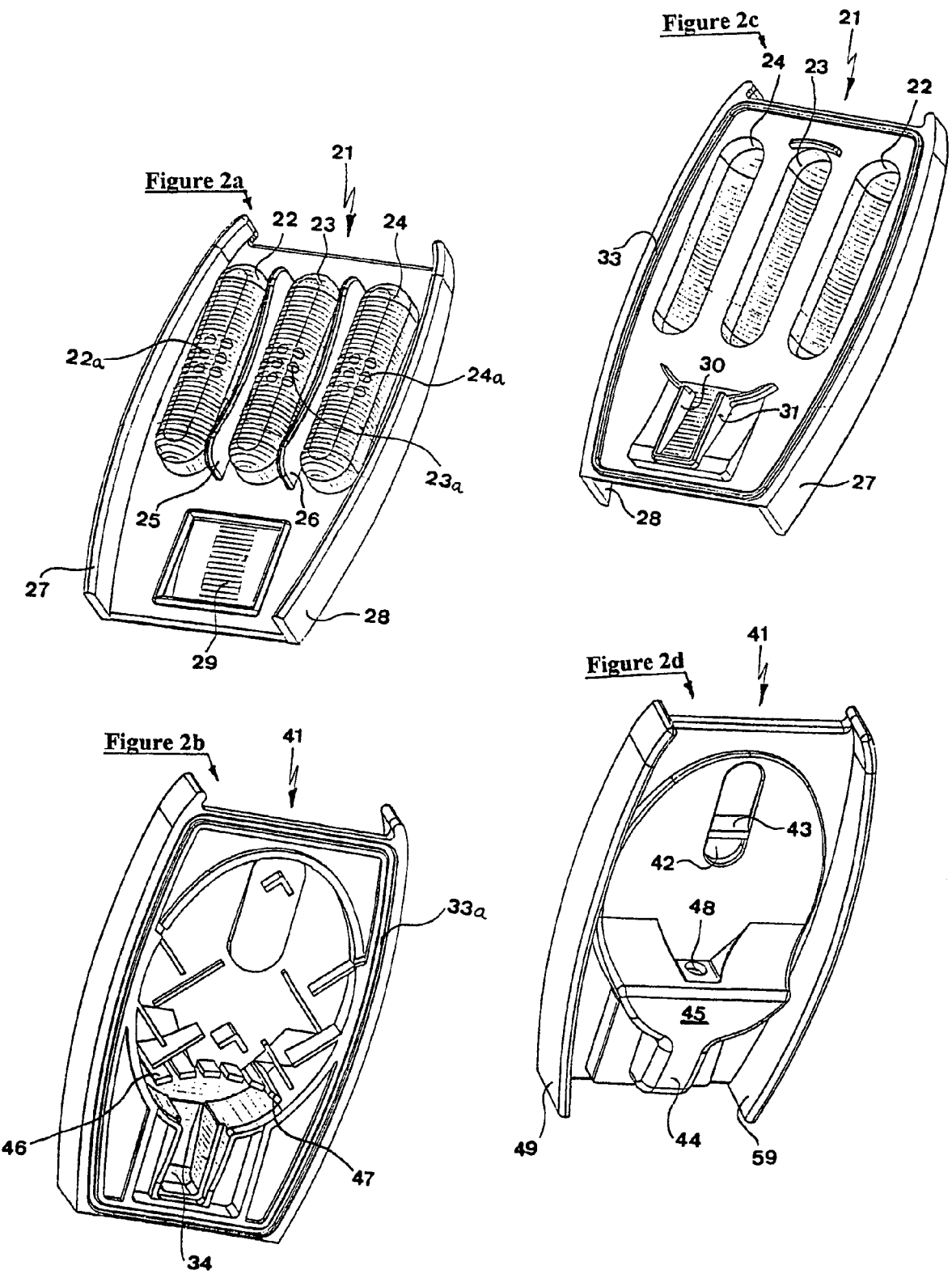

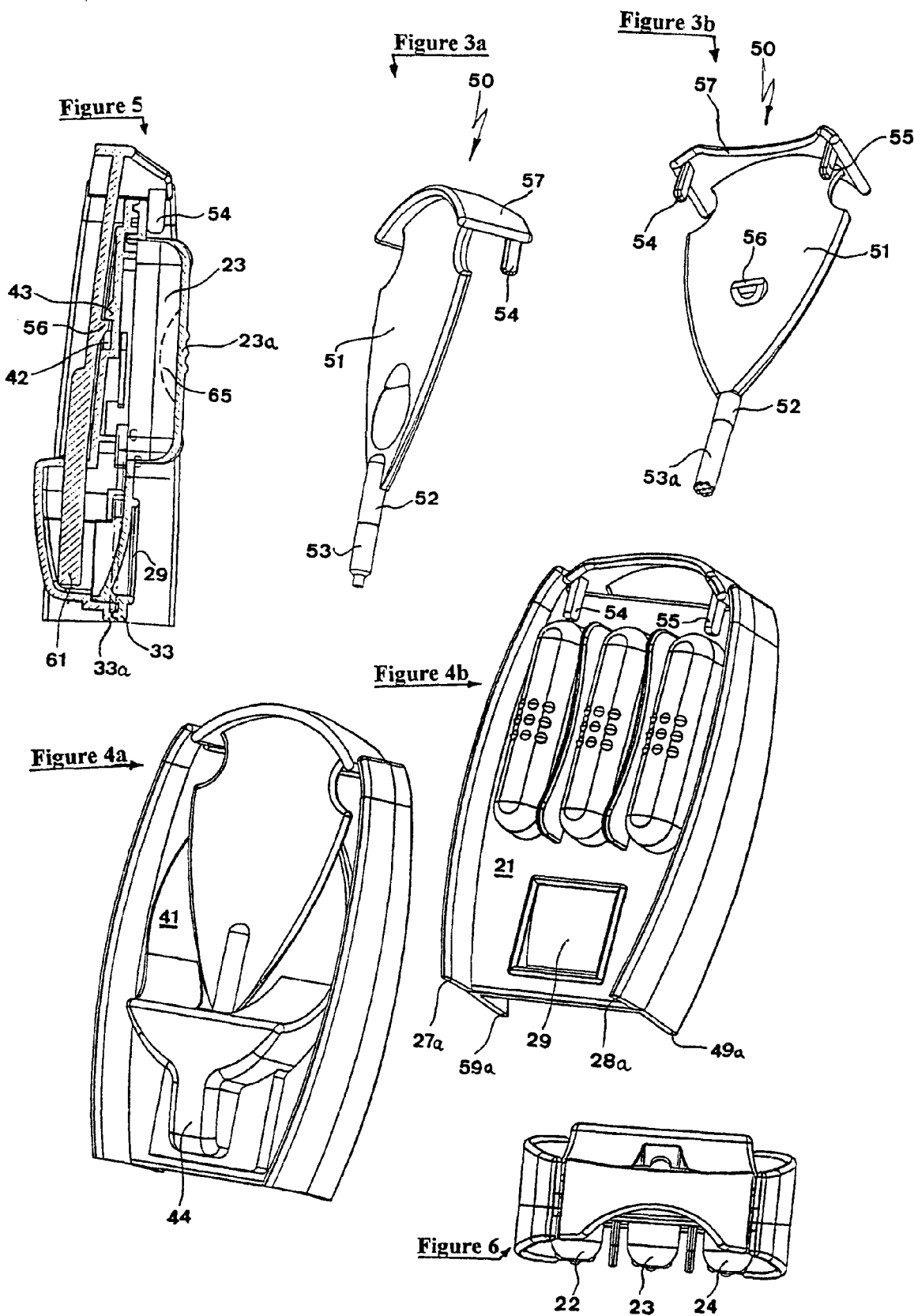

MOLDED CASING FOR A TEST KIT

Figure 1:
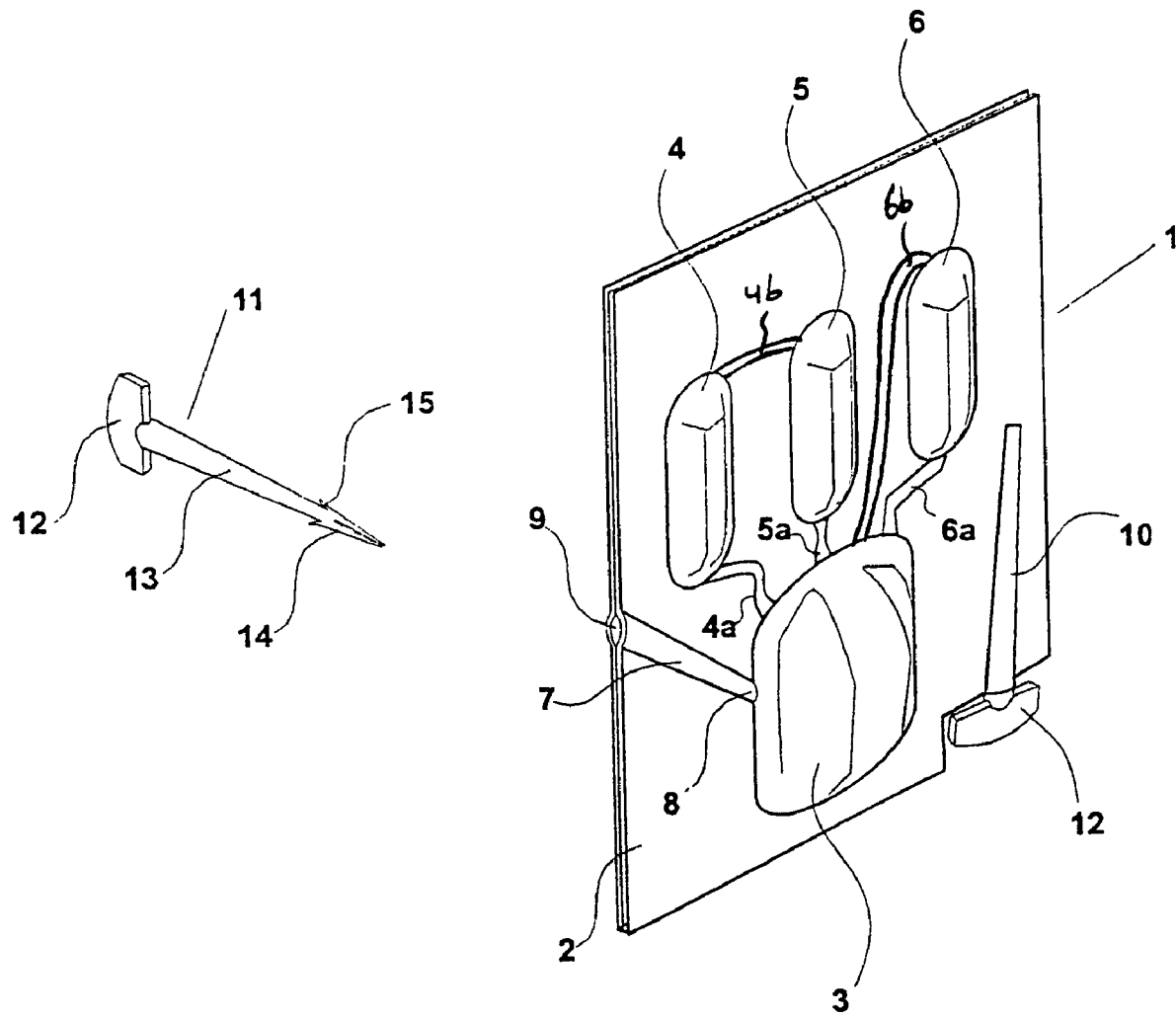

This application is continuation of U.S. patent application No. 09/809,428 filed Mar. 16, 2001 now abandoned.

FIELD OF THE INVENTION

The present invention relates to a molded casing useful as a test kit for chemically or biologically identifying and analyzing the presence of substances (such as illegal drugs). More specifically, the present invention relates to a molded casing having flexible pressable cells (one or more), each adapted to receiving a crushable ampoule pre-filled with a predetermined required chemical or biological reagent or reagents and having a reaction chamber opened to said cells, which also has an inlet for delivering the examined specimen into said reaction chamber, and at least one transparent inspection "window" for observing the results of the reaction carried out in the reaction chamber. Until now, performing such tests was a matter for professionals. The molded casing of the present invention improves and facilitates the performance of the chemical tests, such that unskilled people such as worried parents, school administrators, or employers, can easily and privately check for the presence of drugs. The molded casing according to the present invention is manufactured as a closed disposable unit, thereby ensuring against drain of noxious materials that are involved in some of the chemical tests.

BACKGROUND OF THE INVENTION

A basic problem with glass ampoules used in ampoule-based tests is that, for releasing it's content, there is a need to crush the ampoules which is an unpleasant action. The glass shards of broken ampoules are dangerous to the fingers of the user, and uselessly disperse into the mixture of the reacting materials, disturbing the inspection of the reaction results.

Another problem with ampoule-based tests is that the process of bringing all the involved materials together is slow and toilsome, especially in some kinds of tests which have to be done by using a plurality of ampoules and materials, or by using noxious reagents.

Another problem arises when a test has to be done outdoors or in field conditions. On one hand, the testing ampoules have to be protected, and on the other hand, they have to be ready to use and in a proper composition of materials for the specific test to be made.

The molded casing according to the present invention is especially useful as a testing kit for identifying drugs (such as Cocaine, Heroin, Hashish, Marijuana, Methamphetamine, LSD etc.). In this kind of test, a sample of the material which is suspected of being a drug, has to be mixed with up to three or four different liquids stored in a similar number of small glass ampoules.

The prior art in this field discloses a testing kit, arranged such that a composition of the glass ampoules of the appropriate materials are closed together inside a small plastic pouch, and a sampling tube or toothpick is enclosed as well. Another kind of prior art testing kit is a flexible cigarette-like transparent tube, provided with the required chemicals in sealed pre-filled glass ampoules positioned in a column along the tube, and with a sampling toothpick.

The detection process using said kits is long and cumbersome for people skilled in the art, and it is difficult for use for unskilled people.

The aim of the present invention is to provide a new device enabling fast, facile and clean chemical tests, for the use of unskilled people (worried parents, school administrators, employers etc.) as well as for professionals. The prior art testing kits do not comply with the following, which are the basic requirements for a test kit:
a) ampoules have to be crushed safely and easily.
b) the reaction mixture must be clean from glass shards of broken ampoules.
c) the device has to be insured against fluid leakage.
d) ampoules have to be well-protected in field conditions.
e) sampling of suspected material into the kit has to be fast and easy.
f) the predetermined sequence of crushing the ampoules has to be easily identified by the unskilled user.
h) the device have to include a minimum number of mobile (releasable) parts.
i) each ampoule must be protected from being crushed while crushing other ampoules.
j) the sampled material has to be inserted directly into the test location, without having to tap the device for driving the sample to the place, and for minimizing the possibility of contaminating the sampled material.
k) a convenient background is needed for easily reading the results of a test.

Surprisingly, all said requirements are achieved, in the device of the present invention.

SUMMARY OF THE INVENTION

In the context of the present invention, "test" is any kind of test or chemical or biological reaction, that is performed by mixing at least one tested material (reagent) with at least one other material (reagent) pre-filled in a sealed glass ampoule.

The present invention relates to a casing for use as a test kit using crushable ampoules, comprising a molded casing having a distinct reaction chamber and at least one distinct cell adapted for receiving a crushable ampoule and having a flexible pressing area at its outer wall for pressing and crushing said ampoule, wherein there is an opening between said chamber and said at least one cell, and said opening is narrow enough, or provided with suitable filtering means, to prevent the passage of glass shards from the cell to the chamber. The reaction chamber is further provided with an appropriate inlet opening for the insertion of a sample of tested material, and with a sampling probe for easy placement of the sample inside the reaction chamber, through said inlet.

A reaction between the contents of crushable ampoules and a sample of tested material is produced after crushing the ampoules in the correct sequence and after the required mixture is formed inside said reaction chamber.

The casing can be made from either a casting, injection, vacuum-forming, or press-forming etc. of any appropriate material.

The casing is provided as a closed disposable unit equipped with all the required ampoules inside.

DETAILED DESCRIPTION OF THE INVENTION

The present invention relates to a molded casing useful as a test kit for identifying the presence of substances such as drugs. The casing has flexible, pressable cells (one or more), each adapted for receiving a crushable ampoule filled with a predetermined required chemical reagent (or reagents). Each cell is opened to the reaction chamber, directly or through a short narrow channel. The opening or the channel which connects between a cell and the chamber is either screened, meshed, or built narrower then its associated ampoule, so as to prevent shards of ampoule from passing into the reaction chamber. However, it is wide enough so as to ensure free flow of the ampoule's content from the cell to the chamber. For improved flow, the device may further comprise aeration channels between the cells or between the chamber and cells, for avoiding a bottleneck effect.

The walls of the cells are formed in thickness and flexibility such that crushing the ampoules is easy and safe. At least one portion of an outer wall of each cell is designed to be a "pressing point". This portion is both thin and flexible so as to enable application of sufficient pressure on the inner ampoule for crushing said ampoule to produce a reaction. However, the pressing point is thick enough for protecting the fingers of the user crushing the ampoule, as well as for protecting the ampoule in field conditions. The required flexibility of the pressing point may also be achieved by chocolate bar shaped crossing grooves formed in the casting of the casing material, on the interior surface of the cell wall, behind the pressing point.

The pressing point is located in the wall of a cell for crushing the ampoule at a specific predetermined desired breaking point, preferably against the middle of the ampoule for a complete crush (or according to another variation, near the end of the cell for crushing the round bottom of the ampoule).

Fore easy identification, the pressing points can be marked, i.e. by changing the smoothness (or pattern) of the outer surface of the cells at their pressing points.

For making the crushing action even easier, it is possible to create, at the back side of the cell, two fulcrums, located on opposite ends of the ampoule. In this manner, pressure produced by a user on the pressing point (near the middle of the ampoule, and in the opposite direction to said fulcrums) is given the added advantage of a lever.

According to the preferred embodiment of this invention, if a casing comprises more than one ampoule cell, it further comprises a protective separation barrier between each pair of cells, so as to insure that pressing on one cell for crushing its ampoule, will not cause the (mistaken) crushing of a neighboring ampoule. According to the preferred embodiment of this invention, the casing further comprises side walls having straight bottom ends, thereby enabling positioning the casing vertically on any horizontal surface. The side walls are also useful for protecting the cells in field conditions, in addition to the protection provided by said protective barriers. Another advantage of the side walls is that they may be used as gripping regions for holding the casing by hand during a test procedure.

The casing is further provided with an appropriate inlet opening leading to the reaction chamber. An opening for this purpose may also be a temporarily sealed orifice, having a sealing comprised of a thin layer of material, for being broken and opened at a preferred moment.

It is also possible to design an openable casing (without a fixed opening), for the placement of a sample inside of the reaction chamber by opening the casing itself, and closing it after the sample is placed.

For sampling the tested material, the casing is equipped with a sampling probe, having means for collecting related materials. Such means may be a toothed edge, pronged edge, pincette edge, piped edge, sticky edge or any other efficient means for collecting sample of a specific related material, including means useful for collecting liquid samples (e.g. syringe-like means comprising a miniature piston and a hollow edge, a spongy material edge, or any other means for collecting liquids as known in the art). It is also possible to design a sampling probe with a replaceable end-unit, such that an appropriate end-unit may be adapted for each kind of test from a selection of various shapes and lengths of end-units.

The sampling probe is designed such that it fits into the inlet opening leading to the reaction chamber. The opening of the probe is cone-like, wider at its outer end and narrower at the end that joins with the reaction chamber. The sampling probe has a portion formed with a conforming shape, such that when inserted into the casing in a correct position, the opening is sealed. By such a design, the sampling probe is used also as a sealing cap for the casing, and only two free parts are included in the kit; the casing, and the probe. Thus, the user may easily control the test procedure, without worries about loosing parts.

According to another embodiment of the invention, the sampling probe and the casing have mutual interlocking means such that the probe is locked to the casing, and its removal or insertion requires the application of force to overcome the locking force. The locking means are molded in the body of the probe and the casing, as a protrusion and groove or the like. According to one preferred embodiment of this invention, the locking means are for one time only (irreversible) insertion, such that once a sampling was entered by the probe into the chamber, the probe is locked in the casing, and thus the unit is insured against leakage. Preferably, the casing includes means for gripping the probe before use without lock, thus the kit is supplied to the customer as one unit.

According to one preferred embodiment of this invention, the casing is made from a transparent material, such that it is very easy for a user to observe any color change inside the reaction chamber. Preferably, only predetermined portions ("inspection windows") of the reaction chamber having glossy polishing, while the other portions of the reaction chamber and the casing are opaque (by having a coarse polishing). Thus unskilled people may easily know where to look, for inspecting the color change.

The transparent material has to be resistant against corrosive chemicals that may be involved in the tests. Different variations of polypropylene, which are also very transparent materials, and resistive as required, are suitable.

It is also possible to make the casing from any resistive opaque material, while the reaction chamber is provided with a transparent eyepiece.

The dimensions of the reaction chamber are predetermined and adapted for accommodating the exact quantity of reagents which is expected from a specific test. The sampling probe is also shaped to hold the sample in the exact desired point inside the reaction chamber. The color and shape of the sampling probe can be designed such that the sampling probe provides a convenient background next to the inspection window, for easily viewing the results of a test. Due to all these means, the test is reliable. The casing may be provided to the customer with a color indexing spot printed adjacent to the definite resulting point of the reaction, or printed on a sticker for being adhered there.

It is possible to select any of the above mentioned arrangements and combine them according to the requirements of any specific test, for the manufacturing of a suitable test kit.

The advantages provided by the present invention are as follows:

a) ampoules are crushed safely and easily, and (if necessary) at a predetermined crushing point.

b) the reaction chamber is clean from parts of broken ampoules.

c) the kit is sealed and prevents leakage of fluids during the test procedure.

d) ampoules are protected from harm in field conditions.

e) the sampling of the suspected material into the kit is made fast and easy.

f) crushing of ampoules according to a predetermined order can easily be made (The manufacturer provides each kit with ampoules in their cells in a requested order. The casing may be designed asymmetrically, to avoid mistakes, and/or cells may be marked or numbered according the required order for crushing the associated ampoules.)

g) interlocking means between the sampling probe and the casing prevents leakage of chemicals from the thrown away casing.

h) the user has to handle not more than two separate parts (the casing and the probe)

i) each ampoule is protected from being crushed while crushing other ampoules.

j) the sampled material is inserted directly into the reaction chamber, avoiding loses of material during the insertion, and there is no need to tap the kit for driving the sample to the bottom.

k) the sampling probe provides a convenient background behind the inspection window for easily reading the results of a test.

l) the casing can be positioned vertically on any horizontal surface, with no need to hold it constantly by hand.

The invention will be further described in details by FIG. 1-6. These figures are solely intended to illustrate some preferred embodiments of the present invention, and in no way are meant to limit the scope of the invention.

FIG. 1 describes a test kit (1) for narcotic drug detection, comprising a molded casing (2), with a transparent reaction chamber (3), three cells (4) (5) (6) for ampoules, each ampoule cell being open to the reaction chamber through a channel (4a) (5a) (6a), and a sampling probe (11) provided with the casing in a scabbard (10) (which is one example of gripping means for gripping the probe prior to use), for insertion into a conduit (7) with a sample of suspected material. The conduit (7) is cone shaped, and has a wide opening (9) toward the outer side, and a narrow opening (8) toward the reaction chamber (3). The sampling probe (11) has a cone shaped portion (13), adapted to be inserted through the conduit (7) into the chamber (3), and to seal it. The sampling probe (11) has a gripping handle (12) and a tip (14) having means (the depicted pincette-like means is only one of various possibilities) for collecting a predetermined quantity of the sampled material. The opening (8) from the conduit to the chamber, and the arrow shaped end (15) of the probe, provide mutual irreversible locking means, such that once the probe is fully inserted through the conduit, the arrow shaped end (15) preventing pulling out of the probe. After a sample is inserted, the ampoules are crushed by the user by finger pressing through the walls of cells (4)(5)(6). The liquid of each broken ampoule flows through the associated channel (4a) (5a) (6a) into the reaction chamber (3). The sampled material is now ready for a detection, and the test (reaction) is performed. To improve the flow of reagents from the ampoule cell to the chamber by avoiding a bottleneck effect, aeration channels are provided in the molded casing; (4b) between cells, or (6b) between a cell and the chamber. Since the channels are narrow, the crushed ampoule shards are prevented from reaching the reaction chamber, and the result of the reaction is well inspected through the transparent walls of the chamber (3).

FIG. 2 describes the preferred embodiment of a test kit molded casing according to the present invention. This casing is comprised from two parts (21)(41). FIG. 2a and FIG. 2c, both describe the same part (21). FIG. 2a illustrates its exterior side, and FIG. 2c illustrates its interior side. The other part (41) is illustrated by FIGS. 2b (interior side) and 2d (exterior side). Part (21) of FIG. 2a is configured in position for being attached with part (41) of FIG. 2c. The other side of both parts, is illustrated by FIGS. 2b and 2d. The two parts have rims (33)(33a) for attaching them to each other either by press or by means of ultrasonic soldering.

Part (21) comprises three cells (22)(23)(24) adapted to receive three ampoules (ampoules are not depicted). Pressing points for breaking ampoules (22a) (23a) (24a) are marked in the exterior wall of the cells by a pattern of protruding dots. Rigid separation barriers (25) (26), protrude between the cells for insuring each ampoule from being crushed while crushing a neighboring one. Side walls (27) (28) are also provided, to protect ampoules from harm in field condition and the like.

Part (21) further comprises an observation window (eyepiece) (29) which is also one of the exterior walls of the reaction chamber of the casing, (the horizontal line pattern does not exist in the real test kit, and is provided only to illustrate the actual eyepiece region). The eyepiece is an integral part of the casing, which is all one casting. The eyepiece portion is transparent, due to its glossy polishing.

FIG. 2c illustrates other walls (30) (31) of the reaction chamber. These inner walls reduce the actual inner space of the chamber such that only a mid portion of the observation window is used for observing a reaction (color change) made in the chamber (in these figures, the actual eyepiece region is patterned by horizontal lines). The two excess regions of the observation window (from both sides of said mid portion) may be used for printing (or sticking) color-indexing spots for reading the results of a test in a glance with the index.

Part (41) comprises a main portion of the reaction chamber (44). The reaction chamber is shaped wide at part (45) which is laid open to the ampoule cells (22)(23)(24) when the two parts (21)(41) are attached to each other. The interior side of this wide area of the reaction chamber is illustrated in FIG. 2b, having a filtering screen made of a line of protrusions starts with protrusion (46) which faces the lower end of cell (22), and ends with protrusion (47) which faces the lower end of the opposing cell (24). This filtering screen of spaced protrusions, prevents pieces of broken ampoules from passing into the chamber, but allows free flow of the ampoule content from the cells to the chamber.

The lower part (34) of the chamber is shaped narrow, for focusing the reagents into a distinct region facing the observation window (29). The casing is further comprised of an inlet opening (48) for the insertion of the sampling probe (seen in FIGS. 3a, 3b). The sampling probe is adapted for the placement of a suspected material inside the chamber, at a point facing the observation window. The inlet opening (48) and the sampling probe are contoured such that the opening is sealed by the probe, when the probe reaches its final position inside the chamber. Pit (42) and ramp (43) are parts of mutual interlocking arrangement between the casing and the sampling probe.

FIGS. 3a and 3b, each illustrate the other side of the sampling probe (50). The probe is comprised of a hand grip (57), and a wide body (51) ends with a thin rod (52). The rod (52) has a removable extension (53)(53a), which is the sampling member of the probe. The probes depicted by these two FIGS. (3a and 3b) differ from each other by the type of their sampling members (53)(53a). This difference may be achieved either by designing a main probe and a selection of removable sampling members, or by designing different probes, each with a unique type of sampling member. On the edge of the sampling members (53)(53a) are located collecting means for collecting a sample of suspected material. The collecting means on the edge of the sampling member (53) is a toothed area, to be pressed to a crumb of suspected material for trapping and picking it. The collecting means on the edge of the sampling member (53a) is a miniature hollow cylinder to be pressed to suspected powder remains for picking a sample. The probe further comprises on its wide body (51) an inclined protrusion (56). This protrusion is for locking the probe to the casing, by its mutual interlocking mechanism with said pit (42) (see FIG. 2d). The inclination of the protrusion is for allowing driving the protrusion over said ramp (43) (see FIG. 2d), for being locked into the pit (42).

FIGS. 4a and 4b each illustrate both sides of the complete casing with a sampling probe in position. The mutual interlocking means between casing and probe comprises two projections projecting from the hand grip of the probe, that are held in part (21) of the casing. Those projections, together with the probe rod which is hooked inside of the chamber (44), are secure the protrusion (56) in its conforming pit (42) in part (41) of the casing. Once the probe is fully inserted, there is a "click" made by protrusion (56) slipping from ramp (43) into pit (42). This "click" informs the user that the probe is locked in its position, the reaction chamber is sealed, and the suspected material is placed in front of the observation window. This is the appropriate time to crush the ampoules by pressing the cells in the appropriate sequence. When waiting for the reaction results, the casing can be positioned vertically on a horizontal surface (such a table), due to its wide basis portion, created between the bottom ends (27a)(28a)(59a)(49a) of the side walls (27)(28)(59)(49).

FIG. 5 illustrates a cross section view of the probe positioned and locked in the casing. The end (the tip) (61) of the sampling member is fronting the window (29), the protrusion (56) is locked in pit (42) by the strait end of ramp (43) and by projection (54) which is held from the opposite side of the casing. The dotted patterned pressing point (23a) of cell (23) is ready for pressing it to position (65).

FIG. 6 illustrates a complete view of the casing and the probe from the above.

What is claimed:

1. A casing for use as a test kit using crushable ampoules prefilled with chemical or biological reagents, said casing, which is a molded casing comprising
    a distinct reaction chamber;
    an inspection arrangement constituting at least a portion of a wall of the reaction chamber configured for allowing a user to observe through the casing a color of a reaction inside the reaction chamber;
    at least two distinct cells each adapted to receive a crushable ampoule and having a flexible pressing area on an outer wall thereof for allowing said ampoule to be pressed and crushed;
    at least two channels, each of which connects one of the cells with said reaction chamber for allowing the passage of reagents from the cell to the reaction chamber, wherein each of said channels is built narrower than the respective cell and said reaction chamber thereby preventing shards of crushed ampoules from passing from the cell to the reaction chamber, and
    an inlet leading from an outside of the casing into an inner space of the reaction chamber, wherein the casing is equipped with a sampling probe having a bottom end configured to collect a sample of substance to be tested, to introduce the sample into the reaction chamber through the inlet, and to hold the sample inside the reaction chamber,
    wherein
    the probe and the casing are configured such that, when the probe is fully inserted into the casing, the collected sample is held in a predetermined point in front of the inspection arrangement thereby predetermining a location in front of the inspection arrangement for a color change to occur, and
    said two distinct cells having the ampoules are arranged directly above the reaction chamber so that the chemical or the biological reagents released from the crushed ampoules flow by gravity downward into said reaction chamber via said channels.

2. The casing according to claim 1, wherein said casing is made from either casted, injected, vacuum-formed, or press-formed material.

3. The casing according to claim 1, wherein said casing is provided as a disposable closed unit equipped inside the cells thereof with all the required ampoules for a specific test reaction.

4. The casing according claim 1, further comprising aeration channels between the cells or between the chamber and the cells.

5. The casing according to claim 1, wherein the flexible pressing area at the outer wall of each of the cells is adapted to allow the associated ampoule to be crushed at a specific predetermined breaking point.

6. The casing according to claim 1, further comprising a protective barrier between each pair of said cells, to protect the ampoules from being crushed mistakenly.

7. The casing according to claim 1, wherein the pressing area at the outer wall of each of the cells is marked with a pattern.

8. The casing according to claim 1, wherein the inlet is provided with an one-time-only breakable seal to be punched prior to use.

9. The casing according to claim 1, wherein the sampling probe is a sticky portion for collecting samples by adhesion.

10. The casing according to claim 1, wherein the sampling probe comprises means for collecting liquid samples.

11. The casing according to claim 1, wherein the sampling probe is formed also as a sealing cap to the inlet.

12. The casing according to claim 1, further comprising mutual interlocking means for locking the probe to the casing, wherein said interlocking means are irreversible.

13. The casing according to claim 1, further comprising ampoule fulcrums in at least one of the cells, for reducing the pressing force needed for crushing the ampoule in the cell.

14. The casing according to claim 1, wherein said casing is made of a transparent material having a glossy polishing on at least one of the walls of the reaction chamber.

15. The casing according to claim 1, wherein said casing is made of opaque material, with an eyepiece at the reaction chamber, or with the reaction chamber being made from transparent material.

16. The casing according to claim 1, further comprising a color-indexing spot printed on or applied to a wall of the reaction chamber.

17. The casing according to claim 1, having walls with straight bottom ends, enabling the casing to be positioned vertically on any horizontal surface.

18. The casing according to claim 1, further comprising, together with the sampling probe, means for producing a click when the probe is inserted into the inlet to a predetermined depth.

19. The casing according to claim 1, wherein each said channel connects a lower portion of said respective cell with an upper portion of said reaction chamber to allow a reagent in said ampoule to enter said reaction chamber under gravity when said ampoule is crushed.

20. The casing according to claim 19, further comprising an aeration channel that connects an upper portion of one of said cells with said reaction chamber.

21. The casing according to claim 19, further comprising an aeration channel that connects upper portions of said cells.

* * * * *